US010585029B2

(12) United States Patent
Schladitz et al.

(10) Patent No.: US 10,585,029 B2
(45) Date of Patent: Mar. 10, 2020

(54) ANALYSIS DEVICE FOR DETERMINING PARTICULATE MATTER

(71) Applicant: SICK ENGINEERING GMBH, Ottendorf-Okrilla (DE)

(72) Inventors: Alexander Schladitz, Ottendorf-Okrilla (DE); Kai Klinder, Ottendorf-Okrilla (DE)

(73) Assignee: SICK ENGINEERING GMBH, Ottendorf-Okrilla (DE)

( * ) Notice: Subject to any disclaimer, the term of this patent is extended or adjusted under 35 U.S.C. 154(b) by 0 days.

(21) Appl. No.: 16/227,692

(22) Filed: Dec. 20, 2018

(65) Prior Publication Data
US 2019/0234862 A1   Aug. 1, 2019

(30) Foreign Application Priority Data

Jan. 31, 2018 (EP) .................................. 18154509

(51) Int. Cl.
*G01N 21/00* (2006.01)
*G01N 15/14* (2006.01)
*G01N 15/02* (2006.01)

(52) U.S. Cl.
CPC ..... *G01N 15/1434* (2013.01); *G01N 15/0211* (2013.01); *G01N 2015/1493* (2013.01)

(58) Field of Classification Search
CPC .... G01N 21/53; G01N 21/51; G01N 15/0205; G01N 21/47; G01N 15/1459

(Continued)

(56) References Cited

U.S. PATENT DOCUMENTS 5,104,221 A   4/1992   Bott et al.
5,352,901 A * 10/1994   Poorman .............. G01N 21/532
                                                                 250/574

(Continued)

FOREIGN PATENT DOCUMENTS

DE   10 2012 106 322 B3   10/2013
EP         0493806 A2      7/1992

(Continued)

OTHER PUBLICATIONS

Lisenko, et al., "Nephelometric Method for Measuring Mass Concentrations of Urban Aerosols and their Respirable Fractions", Atmospheric and Oceanic Optics, vol. 27, No. 6, pp. 587-595, 2014.

(Continued)

*Primary Examiner* — Md M Rahman
(74) *Attorney, Agent, or Firm* — Nath, Goldberg & Meyer; Jerald L. Meyer; Stanley N. Protigal

(57) ABSTRACT

An optical analysis device for determining particulate matter includes three light sources having different wavelengths, an apparatus for combining the three transmitted light beams on a common optical path, a measurement volume, an optical axis in the forward scattering direction defines the scattering angle 0°, a light absorption apparatus at 0° that absorbs unscattered light, and six detectors which are arranged at different specified angles which are as close as possible to 0° directly next to the light absorption apparatus, at a second scattering angle between 7° and 40°, at a third scattering angle between 41° and 70°, at a fourth scattering angle between 71° and 115°, at a fifth scattering angle between 116° and 145°, at a sixth scattering angle between 146° and 180°. A control and evaluation unit controls the light sources such that the scattered light is detected in a wavelength selective manner by the detectors.

20 Claims, 2 Drawing Sheets

(58) Field of Classification Search
USPC .......................................................... 356/340
See application file for complete search history.

(56) References Cited

U.S. PATENT DOCUMENTS

| | | |
|---|---|---|
| 2010/0055319 A1 | 3/2010 | Kato et al. |
| 2013/0169953 A1* | 7/2013 | Zordan ................ G01N 21/53 356/72 |
| 2017/0011499 A1 | 1/2017 | Reinhardt |

FOREIGN PATENT DOCUMENTS

| | | |
|---|---|---|
| EP | 0391256 B1 | 1/1994 |
| WO | 2014/065694 A1 | 5/2014 |

OTHER PUBLICATIONS

Gayet, et al., "A new airborne polar Nephelometer for the measurements of optical and microphysical cloud properties. Part I: Theoretical design", Annales Geophysicae, vol. 15, pp. 451-459, 1997.
Search Report dated Apr. 9, 2018 issued in corresponding European Application No. 18154509.6.
Benno, "Lichtstreuung", BNSDOCID: XP_55555642A, Jan. 2, 2003.

* cited by examiner

ANALYSIS DEVICE FOR DETERMINING PARTICULATE MATTER

FIELD

The invention relates to an optical analysis device for determining particulate matter by the method of light scattering.

BACKGROUND

Particulate matter is currently a topical subject. Particulate matter is understood as very small particles whose sizes (aerodynamic diameters) amount to less than 10 µm.

Particulate matter is characterized by $PM_{10}$, $PM_{2.5}$ and $PM_1$. The dust particle size characterized as particulate matter $PM_{10}$ contains 50% of the particles having a diameter of 10 µm, a higher proportion of smaller particles, and a smaller proportion of larger particles. The dust particle size characterized as particulate matter $PM_{2.5}$ contains 50% of the particles having a diameter of 2.5 µm, a higher proportion of smaller particles, and a smaller proportion of larger particles. $PM_{2.5}$ is a subset of $PM_{10}$. The diameter for $PM_1$ is 1 µm.

Since particulate matter carries health risks, it is important to avoid or reduce particulate matter. To be able to take and monitor the correct measures, it is absolutely necessary to know the size distribution of the particular matter and the mass percentages of the particular matter types $PM_{10}$, $PM_{2.5}$ und $PM_1$.

The demands on the determination of particulate matter are increasing all the time since the filter systems of emitting plant such as coal-fired power stations are becoming better and better so that the concentrations are falling; however, at the same time, the limit values are becoming ever stricter, e.g. due to the revision of the directive on national emission ceilings (NEC directive) approved in 2016 that added a commitment for 2030 according to which the German $PM_{2.5}$ emissions have to fall by 43% over 2005 by 2030. Smaller and smaller concentrations therefore have to be determined and analyzed.

Continuously measuring automatic measurement systems (AMS) are used worldwide to monitor particulate emissions or particulate immissions. In practice, an AMS has to be calibrated by means of a gravimetric standard reference method (SRM) at its installation site to convert the information of the AMS only on scattered light into real dust mass concentrations. This calibration becomes more and more difficult with increasing inaccuracy for small dust mass concentrations (~1 $mg/m^3$). Enormous efforts are being made worldwide, e.g. by an artificial increase of the dust concentration by injection of additional dust or by a reduction of the emission control effect, to thus move the values of the SRM measurement above the detection threshold. Alternatively, legislation in Europe permits an extension of the measurement time to better quantify very small dust concentrations or it allows the use of so-called substitutes in exceptional cases whose particle size distribution is very similar to that of the exhaust gas.

It is disadvantageous that these methods do not represent any real solutions for the measurement problem since they on the contrary increase the costs for the system operator for the initial calibration or for the regular functional test. In addition, it is not possible to obtain any size-resolved information on the dust concentration with current AMS.

An analysis device is known from EP 0 391 256 B1 for determining a particle size distribution in which the 90° scattered light technology is used. The particle size is determined using laterally scattered light. The scattered light is detected and is measured as a voltage signal. A conclusion can be drawn on a particle size from the voltage signal by means of a calibration function. The number of particles is obtained via the same signal in that pulses of the signal are counted. The particle mass concentration separated by particle size is calculated by volume integration of the measured particle number size distribution curve.

The greatest disadvantage of this 90° scattered light technology is that the scattered light of single particles is measured. Single particles are required for this purpose that have to be present in the measurement volume and thus have to be introduced into the measurement volume as single particles. This is laborious and additionally brings about further problems such as low partial pressures and a supply of carrier gas (for dilution) and thus a possible falsification of the measurement results.

A further technology for particle size analysis is laser light diffraction (laser diffraction technology). The interaction of laser light with particles produces characteristic scatter patterns. These scatter patterns depend on the particle size, on the optical properties of the particles, on the dispersion, and on the wavelength of the incident light. Large particles scatter light more in the direction of small scattering angles. An analysis device therefore requires a high resolution in the forward direction, but also in the direction of large scattering angles for light scattered laterally and back. A known analyzer is the HORIBA LA-960 that has a multi-element ring detector in the forward direction and a plurality of further single detectors toward the side and in the rearward direction and thus detects large areas of the total measurement region. In addition two light sources having different wavelengths (650 nm and 405 nm) are used, whereby the sensitivity for smaller particles (nanoparticles) is increased.

The greatest disadvantage of laser diffraction technology is that the device does not output any absolute particle size distribution (in physical units, e.g. $µg/m^3$). Such devices instead deliver a relative size distribution function and a cumulative size distribution from 0 to 100%. Neither a particle mass concentration nor mass percentages of the particular matter, i.e. $PM_1$, $PM_{2.5}$ or $PM_{10}$, can thus be obtained.

SUMMARY

Starting from this prior art, it is the object of the invention to provide an improved analysis device with which the aforesaid disadvantages can be avoided.

This object is achieved by an optical analysis device or determining particulate matter, in which at least three light sources transmit corresponding light beams having different wavelengths. The three transmitted light beams are combined on a common optical path. A measurement volume into which gas Charged with particulate matter can be introduced and in which the transmitted light is incident on the gas to be measured and is scattered at the articulate matter and a center is defined in the measurement volume from where scattering angles (α) are defined, and the optical axis in the forward scattering direction defines the scattering angle 0°. A light absorption apparatus at 0° detects unscattered light. A first detector is arranged as close as possible to 0° directly next to the light absorption apparatus detects scattered light in the forward direction. A second detector is arranged at a second scattering angle between 7° and 40°. A third detector is arranged at a third scattering angle between 41° and 70°. A fourth detector is arranged at a fourth scattering angle between 71° and 115°. A fifth detector is arranged at a fifth scattering angle between 116° and 145°. A sixth detector is arranged at a sixth scattering angle between 146° and 180°. The detectors detect scattered light at the respective angles. A control and evaluation unit controls the light sources such that the scattered light is detected in a wavelength selective manner by the detectors, and a memory stores the detected scattered light intensities. The control and evaluation unit is configured such that the size distribution of the particular matter and the particular matter mass percentages can be determined from the scattered light intensities.

The analysis device in accordance with the invention comprises
- three light sources for transmitting three transmitted light beams having different wavelengths;
- an apparatus for combining the three transmitted light beams on a common optical path;
- a measurement volume into which gas charged with particulate matter can be introduced and in which the transmitted light is incident on the gas to be measured and is scattered at the particulate matter, and a center is defined in the measurement volume from where scattering angles are defined, with the optical axis in the forward scattering direction defining the scattering angle 0°;
- a light absorption apparatus at 0° that detects unscattered light;
- a first detector that is arranged as close as possible to 0° directly next to the light absorption apparatus (smallest possible angle depending on dimensions typically 6°) and that detects scattered light in the forward direction;
- a second detector that is arranged at a second scattering angle between 7° and 40°;
- a third detector that is arranged at a second scattering angle between 41° and 70°;
- a fourth detector that is arranged at a fourth scattering angle between 71° and 115°;
- a fifth detector that is arranged at a fifth scattering angle between 116° and 145°;
- a sixth detector that is arranged at a sixth scattering angle between 146° and 180° so that the detectors detect scattered light at the respective angle;
- a control and evaluation unit that controls the light sources such that the scattered light is detected in a wavelength-selective manner by the detectors;
- a memory for storing the detected scattered light intensities;
- and the control and evaluation unit is configured such that the size distribution of the particular matter (PSD) and the particular matter mass percentages (PM) can be determined from the scattered light intensities.

The invention combines these features with some advantages of the 90° scattered light technology of laser diffraction technology, but with the described disadvantages being avoided. In particular
- three different wavelengths (e.g. one in the UV range, one in the visible range, and one in the near infrared range) are in particular used to further increase the detection probability of smaller particles, e.g. from combustion processes;
- linear polarized light is used, whereby the calculation of the particle size distribution from the measured scattered light intensities can be improved;
- an absolute detector signal calibration can take place by means of reference particles having a known particle size distribution; and
- a plurality of detectors are used in the front-scattering, sideward-scattering and back-scattering directions, whereby the scattered signal pattern can be better detected and so that smaller particles from combustion processes can be detected.

The particulate matter mass percentages $PM_1$, $PM_{2.5}$, and $PM_{10}$ and the total dust concentration can be measured continuously using the analysis device in accordance with the invention.

The angular positions of the detectors represent the key to the invention. The advantages can only be achieved with at least six detectors in said angular ranges. The angular ranges were found in that the set of detector positions at which maximum differences occur in the detector signals was calculated using artificial particles having a known particle shape and a known size distribution so that in normal operation different size distributions can then be ideally distinguished from one another and so that thus what is described in even more detail further below can be determined.

It was found in this respect that ideal results are achieved if
- the first scattering angle is between 0° and 6°;
- the second scattering angle is between 23° and 33°, in particular at approximately 28°;
- the third scattering angle is between 56° and 66°, in particular at approximately 61°;
- the fourth scattering angle is between 91° and 101°, in particular at approximately 96°;
- the fifth scattering angle is between 125° and 135°, in particular at approximately 128°; and
- the sixth scattering angle is between 145° and 165°, in particular at approximately 155°.

The transmitted light beams can thus, for example, be expanded and can have a diameter of approximately 4 mm in the region of the measurement volume. The measurement volume is thereby correspondingly large so that a higher scattered light yield is possible that improves the detection threshold toward small mass concentrations.

BRIEF DESCRIPTION OF THE DRAWINGS

The invention will be explained in detail in the following with reference to embodiments and to the drawing. There are shown in the drawing.

DETAILED DESCRIPTION

Figure 1:
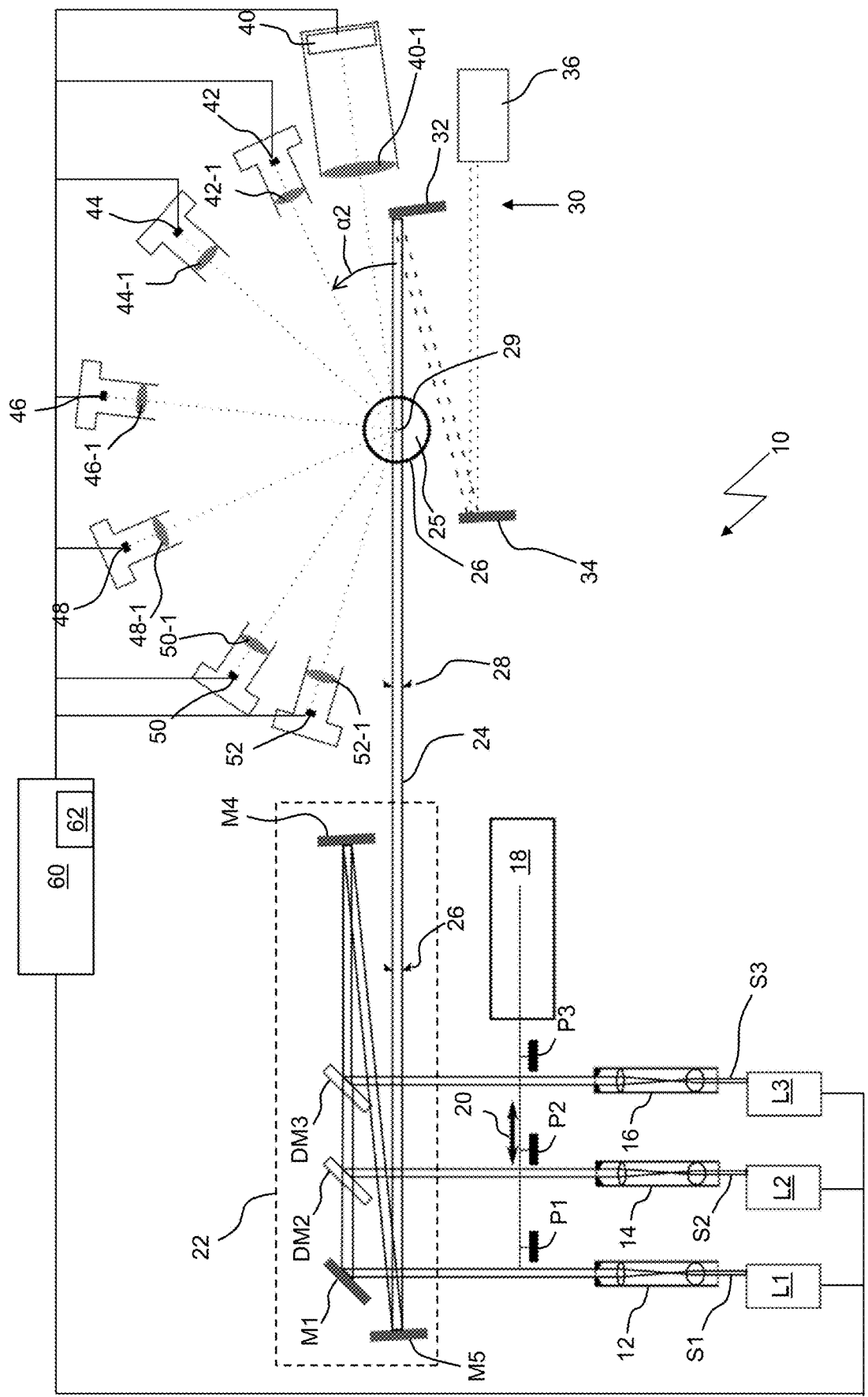
FIG. 1 a schematic representation of the analysis device in accordance with the invention.

An analysis device 10 in accordance with the invention shown in FIG. 1 comprises three light sources L1, L2, L3 that are preferably configured as diode lasers and that transmit transmitted light beams S1, S2, S3 in bundles. The wavelengths of the three diode lasers differ and are preferably in the UV range or visible range or near infrared range. In this embodiment, the first transmitted light beam has a wavelength in the range from 600 to 650 nm, the second transmitted light beam S2 has a wavelength in the range from 900 to 950 nm, and the third transmitted light beam S3 has a wavelength in the range from 400 to 450 nm. Each transmitted light beam S1, S2, S3 is expanded in diameter to preferably approximately 4 mm in a respective beam expander 12, 14, 16. The beam expanders 12, 14, 16 each comprise one lens having a short focal length and one lens having a long focal length, and a diaphragm.

100% of the transmitted light is linearly polarized by means of polarizing filters P1, P2, P3 whose polarization directions are aligned the same, with the polarization direction being horizontal to the plane of the drawing of FIG. 1, that is horizontal to the scatter plane in which the detectors explained further below are disposed. The polarizing filters P1, P2, P3 can optionally be removed from or introduced into the beam paths by means of an actuator 18 in the direction 20.

The still separate beam paths S1, S2, S3 are combined to a common optical path 24 in an apparatus 22. The apparatus 23 comprises a plurality of mirrors in the embodiment of FIG. 1. A first highly reflective silver-coated mirror M1 deflects the first transmitted light beam S1 by 90°. Dichroitic second and third mirrors DM2 and DM3 are transparent for the first light beam S1. The second light beam S2 is likewise deflected by 90° by the second mirror DM2 so that the first and second transmitted light beams are on a common optical path. The beam combination takes place in accordance with the same principle at the third mirror DM3 so that all three transmitted light beams are on the same optical path. Two further mirrors M4 and M5 finally guide the transmitted light beams that are on the common optical path into a measurement volume 25, with light that is not on the optical axis and is therefore interfering being blocked by means of diaphragms 26 and 28.

The measurement volume 26 is defined by the transmitted light beams S1, S2, S3 that transverse a cuvette on the same optical path 24. The cuvette serves to lead through gas to be measured and containing particulate matter particles. A center 29 from where scattered light angles α are defined is defined in the measurement volume 25, with the scattered light being generated by light scattering at the particulate matter particles. The zero point of the scattered light angles is defined here by the optical axis (the common optical path) in the forward scattering direction.

The unscattered light that would interfere with a measurement of scattered light, as depicted in the embodiment shown, is absorbed in three stages in a light absorption apparatus 30. The unscattered light is first led at 0° to a neutral density filter 32 that has a high optical density and only reflects approximately 0.001%. The residual light reflected in this manner is incident onto a second neutral density filter 34 having the same optical density. The light then still remaining is absorbed in a light trap 36.

Detectors for detecting scattered light are arranged around the center 29 at specific scattered light angles α in a common plane, this is the plane of the drawing in the embodiment of FIG. 1.

A first detector 40 is arranged as closely as possible to 0°. Since the transmitted light beams have a certain width, 4 mm here, and since the light not subject to interference is incident below 0° and this has to be absorbed by the light absorption apparatus 30, the first detector 40 is arranged directly next to the absorbing neutral density filter 32 that itself has a certain extent. A typical smallest scattering angle that is possible due to these geometries is in the range from α=6°. This first detector 40 thus detects scattered light in the forward direction. The first detector 40 can be a simple photodetector and is, however, preferably configured as an integrating CMOS line sensor with, for example, 2048 pixels.

Further detectors are arranged as follows:
a second detector 42 at a second scattering angle α2 between 7° and 40°, preferably between 23° and 33°, and in particular at approximately 28°;
a third detector 44 at a third scattering angle α3 between 41° and 70°, preferably between 56° and 66°, and in particular at approximately 61°;
a fourth detector 46 at a fourth scattering angle α4 between 71° and 115°, preferably between 91° and 101°, and in particular at approximately 96°;
a fifth detector 48 at a fifth scattering angle α5 between 116° and 145°, preferably between 125° and 135°, and in particular at approximately 128°; and
a sixth detector 50 at a sixth scattering angle α6 between 146° and 180°, preferably between 145° and 165°, and in particular at approximately 155°.

A seventh detector 52 is preferably arranged at a seventh scattering angle range α7 between 166° and 180°, in particular at 170°. The fifth, sixth, and seventh detectors therefore measure in the backscattering direction.

A reception optics 40-1, 42-2, 44-1, 46-1, 48-1, 50-1 and 52-1 is associated with each detector; it respectively detects the scattered light from a scattering angle tolerance range of approximately +/−1° and focuses it on the respective detector so that e.g. when the detector 44 is arranged at 61°, it can detect the scattered light that is emitted into the angular range from 60° to 62°.

The analysis device 10 further comprises a control and evaluation unit 60 that, on the one hand, controls the light sources L1, L2, L3 and, on the other hand, records the detector signals and carries out the evaluation from them by means of suitable algorithms and ultimately determines the size distribution of the particular matter (particle size distribution PSD) and determines the particulate matter mass percentages (that is the PMx values). A control of the light sources is necessary to be able to detect the scattered light in a wavelength-selective manner using the detectors 40 to 52. A memory 62 for storing the detected scattered light intensities is required for the evaluation in the evaluation unit 60.

The angular ranges or the angular positions of the detectors represent the key to the invention. They were found in that the set of detector positions at which maximum differences occur in the detector signals was calculated using artificial particles having a known particle shape and a known size distribution so that in normal operation different size distributions can then be ideally distinguished from one another and can thus be determined. The differential scatter cross-sections were calculated for this purpose for 105 particle shapes and 9 different size distributions and three different wavelengths in the angular range from 0° to 180°. A calculation was finally made as to the set of six detector angles at which the best result occurs, that is the aforesaid maximum differences in the detector signals.

The result can be found in the above-named detector angle ranges or detector angles α.

The amplified detector signals are calibrated to physical units (differential scatter coefficient) by means of test particles having a known size distribution and known optical properties.

A particle size distribution is determined from the differential scatter cross-sections in the evaluation unit 60 based on stored algorithms and algorithms known from scatter theory for the used three wavelengths (for example, 450 nm, 638 nm, and 915 nm). And finally the particulate matter mass percentages $PM_1$, $PM_{2.5}$, and $PM_{10}$ and the total particle mass concentration are obtained from the particle size distribution by corresponding integration over the particle size.

The particle size distribution and the particulate matter mass percentages $Pm_x$ can thus be continuously determined by absolute calibration using the analysis device in accordance with the invention. The determination of the particle size distribution is therefore based on algorithms and is thus advantageously independent of the kind of particles.

Figure 2:
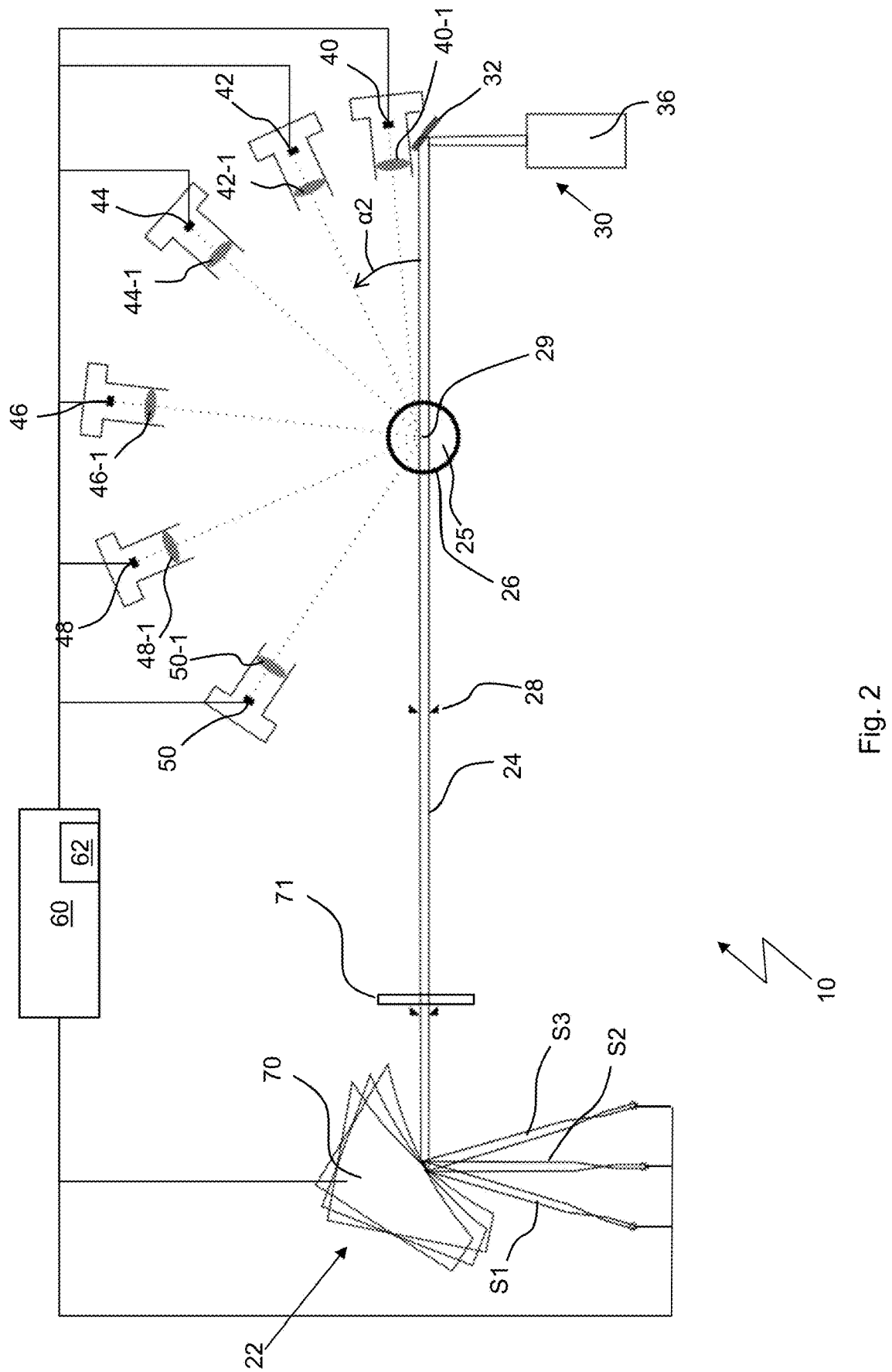
FIG. 2 a further embodiment of the analysis device.

In another embodiment, the above-described first detector 40, that is configured as a CMOS line sensor there, can be configured as a high-sensitivity photodetector that should be shielded by a neutral density filter to intercept the incident laser light and diffraction effects that arise due to beam-bounding diaphragms. This is indicated in FIG. 2. The light absorption apparatus 30 can then possibly also be designed more simply due to the better space relationships, e.g. by only one neutral density filter 32 and the light trap 36.

In an embodiment of the invention likewise shown in FIG. 2, the apparatus for the beam combination 22 is not implemented with fixed-position mirrors, but rather by means of a pivotable parabolic mirror 70 that is then controlled by the control and evaluation unit 60 and that can guide each of the three light beams S1, S2, S3 to the one optical path 24 depending on the pivot angle position. Such an apparatus 22 having a pivotable parabolic mirror 70 requires less construction space and fewer optical components. The light that is transmitted by the laser diodes and that is polarized differently and in a non-defined manner is linearly polarized horizontally to the scatter plane by means of a broadband wire grid polarizer 71.

The invention claimed is:

1. An optical analysis device (10) for determining particulate matter, said optical analysis device (10) comprising,
   three light sources (L1, L2, L3) for transmitting three transmitted light beams (S1, S2, S3) having different wavelengths;
   an apparatus (22) for combining the three transmitted light beams (S1, S2, S3) on a common optical path (24);
   a measurement volume (25) into which gas charged with particulate matter can be introduced and in which the transmitted light (S1, S2, S3) is incident on the gas to be measured and is scattered at the particulate matter and a center (29) is defined in the measurement volume from where scattering angles (α) are defined, with the optical axis in the forward scattering direction defining the scattering angle 0°;
   a light absorption apparatus (30) at 0° that detects unscattered light;
   a first detector (40) that is arranged as close as possible to 0° directly next to the light absorption apparatus (30) and that detects scattered light in the forward direction;
   a second detector (42) that is arranged at a second scattering angle between 7° and 40°;
   a third detector (44) that is arranged at a third scattering angle between 41° and 70°;
   a fourth detector (46) that is arranged at a fourth scattering angle between 71° and 115°;
   a fifth detector (48) that is arranged at a fifth scattering angle between 116° and 145°;
   a sixth detector (50) that is arranged at a sixth scattering angle between 146° and 180° so that the detectors detect scattered light at the respective angle;
   a control and evaluation unit (60) comprising a computer and memory that controls the light sources (L1, L2, L3) using algorithms such that the scattered light is detected in a wavelength selective manner by the detectors (40, 42, 44, 46, 48, 50);
   a memory (62) for storing the detected scattered light intensities;
   and the control and evaluation unit (60) using algorithms to ultimately determine the size distribution of the particular matter and the particular matter mass percentages from the scattered light intensities.

2. The analysis device in accordance with claim 1, characterized in that
   the first scattering angle is between 0° and 6°;
   the second scattering angle is between 23° and 33°;
   the third scattering angle is between 56° and 66°;
   the fourth scattering angle is between 91° and 101°;
   the fifth scattering angle is between 125° and 135°;
   the sixth scattering angle is between 145° and 165°.

3. The analysis device in accordance with claim 2, characterized in that a seventh detector is arranged in a seventh scattering angle range between 166° and 180° C.

4. The analysis device in accordance with claim 2, characterized in that the transmitted light is linearly polarized.

5. The analysis device in accordance with claim 2, characterized in that the first detector is configured as a CMOS line sensor.

6. The analysis device in accordance with claim 2, characterized in that each detector has an optics that detects the light from a scattered light tolerance range of +/−1° and focuses it on the detector.

7. The analysis device in accordance with claim 2, characterized in that the apparatus for beam combination is either implemented with fixed-position mirrors or has a pivotable parabolic mirror that can conduct the transmitted light of each of the three light sources on the one optical path in dependence on the pivot angle position.

8. The analysis device in accordance with claim 2, characterized in that the wavelengths of the light sources are in the ultraviolet range, visible range, and infrared range.

9. The analysis device in accordance with claim 2, characterized in that the transmitted light beams are expanded and have a diameter of approximately 4 mm in the region of the measurement volume.

10. The analysis device in accordance with claim 2, characterized in that the amplified detector signals are calibrated to physical units by means of test particles having a known size distribution and known optical properties.

11. The analysis device in accordance with claim 1, characterized in that
    the first scattering angle is between 0° and 6°;
    the second scattering angle is approximately 28°;
    the third scattering angle is approximately 61°;
    the fourth scattering angle is approximately 96°;
    the fifth scattering angle is approximately 128°; and
    the sixth scattering angle is approximately 155°.

12. The analysis device in accordance with claim 11, characterized in that a seventh detector is arranged in a seventh scattering angle range between 166° and 180° C.

13. The analysis device in accordance with claim 11, characterized in that a seventh detector is arranged in a seventh scattering angle range of approximately 170°.

14. The analysis device in accordance with claim 11, characterized in that the transmitted light is linearly polarized.

15. The analysis device in accordance with claim 11, characterized in that the first detector is configured as a CMOS line sensor.

16. The analysis device in accordance with claim 11, characterized in that each detector has an optics that detects the light from a scattered light tolerance range of +/−1° and focuses it on the detector.

17. The analysis device in accordance with claim 11, characterized in that the apparatus for beam combination is either implemented with fixed-position mirrors or has a pivotable parabolic mirror that can conduct the transmitted light of each of the three light sources on the one optical path in dependence on the pivot angle position.

18. The analysis device in accordance with claim 11, characterized in that the wavelengths of the light sources are in the ultraviolet range, visible range, and infrared range.

19. The analysis device in accordance with claim 11, characterized in that the transmitted light beams are expanded and have a diameter of approximately 4 mm in the region of the measurement volume.

20. The analysis device in accordance with claim 11, characterized in that the amplified detector signals are calibrated to physical units by means of test particles having a known size distribution and known optical properties.

* * * * *